(12) United States Patent
Taft

(10) Patent No.: US 6,764,492 B2
(45) Date of Patent: Jul. 20, 2004

(54) BONE IMPACTION INSTRUMENT

(75) Inventor: Richard J. Taft, Austin, TX (US)

(73) Assignee: Zimmer Technology, Inc., Chicago, IL (US)

( * ) Notice: Subject to any disclaimer, the term of this patent is extended or adjusted under 35 U.S.C. 154(b) by 205 days.

(21) Appl. No.: 09/949,744

(22) Filed: Sep. 10, 2001

(65) Prior Publication Data

US 2003/0050643 A1 Mar. 13, 2003

(51) Int. Cl.⁷ .............................................. A61B 17/56
(52) U.S. Cl. ...................................................... 606/86
(58) Field of Search ............................. 606/86, 92, 93, 606/99, 100; 623/20.16, 20.32, 20.35, 22.12, 23.15, 23.48, 23.46

(56) References Cited

U.S. PATENT DOCUMENTS

| | | | |
|---|---|---|---|
| 5,403,320 A | | 4/1995 | Luman et al. |
| 5,443,471 A | * | 8/1995 | Swajger ........................ 606/99 |
| 5,464,406 A | | 11/1995 | Ritter et al. |
| 5,601,567 A | * | 2/1997 | Swajger et al. ............. 606/102 |
| 5,766,261 A | * | 6/1998 | Neal et al. ................ 623/21.15 |
| 5,776,261 A | | 7/1998 | Panyard et al. |
| 5,910,172 A | * | 6/1999 | Penenberg ............... 623/23.21 |
| 5,931,841 A | | 8/1999 | Ralph |
| 6,120,509 A | | 9/2000 | Wheeler |
| 6,126,694 A | * | 10/2000 | Gray, Jr. ................... 623/22.11 |
| 6,127,596 A | | 10/2000 | Brown et al. |
| 6,149,687 A | * | 11/2000 | Gray et al. .............. 623/20.34 |
| 6,238,435 B1 | * | 5/2001 | Meulink et al. .......... 623/22.12 |
| 6,432,110 B1 | * | 8/2002 | Richelsoph ................... 606/62 |
| 6,524,344 B2 | * | 2/2003 | Yoon ....................... 623/23.46 |

* cited by examiner

Primary Examiner—Kevin Shaver
Assistant Examiner—Michael B. Priddy
(74) Attorney, Agent, or Firm—Jonathan D. Feuchtwang; Zimmer Technology, Inc.

(57) ABSTRACT

A technique for preparing a bone to receive an implantable orthopedic component. The technique utilizes a modular bone impaction preform. The preform holds the shape of the implantable component during impaction of bone replacement material to fill defects formed in the bone via disease, congenital defect, or trauma. Typically, the bone impaction preform is used with an instrument that may comprise a trial stem, a trial stem adapter, and a handle. The bone impaction preform and trial stem, as well as the other components, can be made in modular form to facilitate interchangeability.

6 Claims, 9 Drawing Sheets

BONE IMPACTION INSTRUMENT

FIELD OF THE INVENTION

The present invention relates generally to the implanting of orthopedic prostheses for replacing portions of skeletal joints, and more particularly, to surgical instruments and their use in preparing bones to receive implantable orthopedic prostheses.

BACKGROUND OF THE INVENTION

Implant able orthopedic prostheses, in one form, comprise man-made replacements for the ends and articulating surfaces of the bones of the skeleton. Such prostheses are implanted to repair or reconstruct all or part of an articulating skeletal joint that is functioning abnormally due to disease, trauma, or congenital defects. Among the various articulating skeletal joints of the human body, for example, that are eligible to be fitted with implantable orthopedic prostheses, the knee, hip, and shoulder joints are often beneficial recipients.

The hip and knee joints play an important role in ambulation, and the shoulder joint plays an important role in manual dexterity. This results in great demand for surgical correction of abnormalities in these joints, and the ability to correct such abnormalities can have an important affect on the quality of life.

As used herein, the words proximal and distal are terms of reference that indicate a particular portion of a bone or prosthesis component according to the relative disposition of the natural bone or implanted prosthesis. Proximal indicates that portion of a component nearest the torso, whereas distal indicates that portion of a component farthest from the torso.

In a variety of implantation procedures, the bone receiving a prosthetic component is initially prepared for receipt of that component. For example, certain prosthetic components include a stem and an expanded boss that are placed into the medullary canal of the subject bone, e.g., the proximal end of a tibia prepared for receipt of a prosthetic knee joint component having a stem and a tibial boss. Preparation of the bone includes reaming the medullary canal to a size and shape able to receive the stem and expanded boss of the prosthetic component. This surrounding bone tissue supports the prosthetic component.

Prior to insertion of the stem, a trial stem is inserted into the reamed region to ensure a proper fit of the prosthetic component. In some procedures, the trial stem remains in the reamed cavity during additional cuts that are made to properly shape the bone. In fact, the trial stem can be used to support cutting instruments utilized in shaping the end of the bone for receipt of the prosthetic component.

In some cases, disease, congenital defect, or trauma can create voids in the bone tissue at a location where bone tissue is required to support the implant component. For example, certain degenerative diseases can lead to the formation of a cavity at the proximal end of the tibia or at other joint locations that could benefit from the implantation of a prosthetic device. Such voids, whether cavity or non-cavity voids, must be repaired in such a manner that will allow tissue to attach to the component and provide support for the prosthetic component.

A variety of bone replacement materials, such as allograft bone, autograft bone, bone graft substitutes, bone matrix, and suitable biological products may be used to repair voids or other defects in the bone tissue. The bone replacement material is impacted into the contained or uncontained defect to bond with and support the implanted prosthetic component. During this impaction procedure, it would be desirable to prevent the impacted bone from falling into the medullary canal or other areas that will be occupied by the prosthetic component upon implantation. It also would be desirable to provide for proper formation of the bone replacement material so as to accommodate receipt of the prosthetic component.

SUMMARY OF THE INVENTION

The present invention provides a technique for preparing a bone to receive an implantable orthopedic prosthesis. In one embodiment, the technique comprises the use of a bone impaction preform to hold the shape of an implantable component during impaction of the bone replacement material. In this embodiment, the bone impaction preform is a modular component that may be selectively coupled and uncoupled with a trial stem and/or a trial stem adapter.

In modular form, a variety of bone impaction preforms and trial stems can be combined according to the type and size of the joint being prepared for receipt of an implantable orthopedic prosthesis. With this modularity, a relatively small number of trial stems and modular preforms can be combined in a relatively large number of configurations. In one exemplary application of the present technique, a practitioner selects a desired combination of a modular trial stem in a modular preform. The inner region or medullary canal of a bone is then reamed to sufficient size to accommodate the stem of an implantable prosthetic component. The modular trial stem is moved into the reamed canal until the modular preform is at least partially positioned within the void to be prepared. Once positioned, bone replacement material is readily packed around the modular preform. The modular preform prevents bone replacement material from falling into the medullary canal while holding the shape of the component to be implanted.

BRIEF DESCRIPTION OF THE DRAWINGS

The invention will hereafter be described with reference to the accompanying drawings, wherein like reference numerals denote like elements, and.

DETAILED DESCRIPTION OF EXEMPLARY EMBODIMENTS

Figure 1:
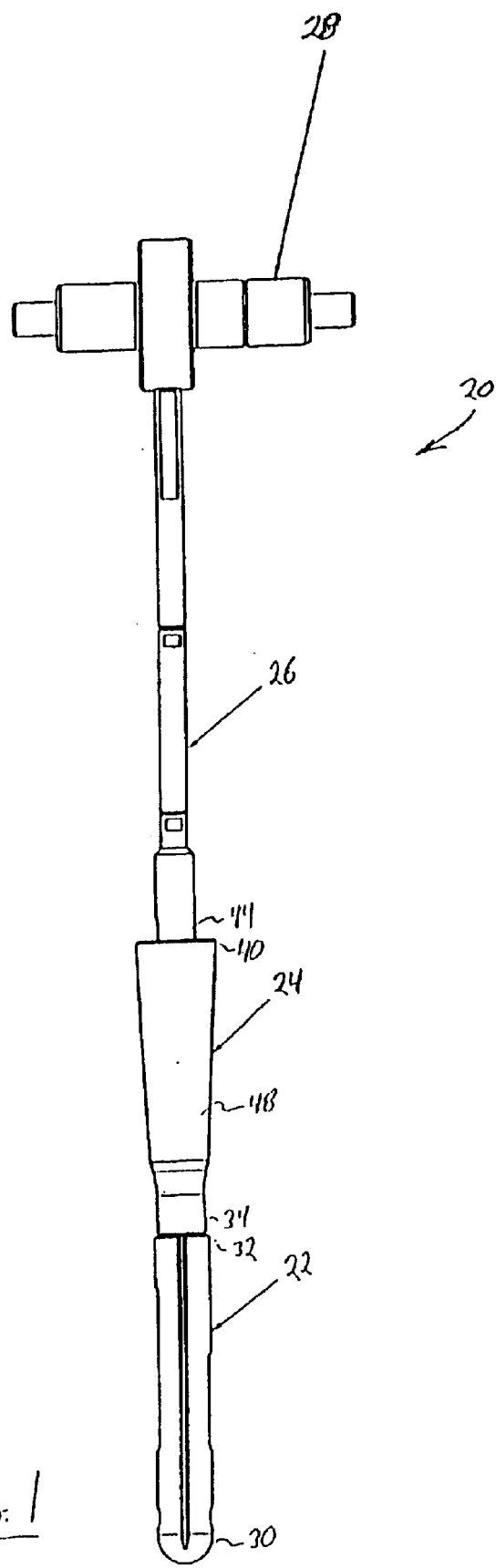
FIG. 1 is a front view of a bone impaction instrument, according to one embodiment of the present invention.

Referring generally to FIG. 1, a bone impaction instrument 20 is illustrated according to one embodiment of the present invention. Although the embodiment illustrated is designed for use in the proximal tibial region during implantation of an orthopedic prosthesis at the knee joint, the selection of this design is to facilitate explanation and should not be construed as limiting. For example, similar bone impaction instruments 20 can be designed for use at the proximal or distal ends of the femur, proximal or distal ends of the humerus, one or more ends of the ulna, and potentially at other joint locations by appropriately modifying the shape and size of the instrument.

In the embodiment illustrated, bone impaction instrument 20 comprises a trial stem 22, a bone impaction instrument or preform 24, a trial stem adapter 26, and a handle 28. Each of these components can be constructed from a suitable, biocompatible material, such as surgical stainless steel. In this embodiment, trial stem 22, bone impaction preform 24, trial stem adapter 26, and handle 28 are modular in form to allow the interchange of components.

Figure 2:
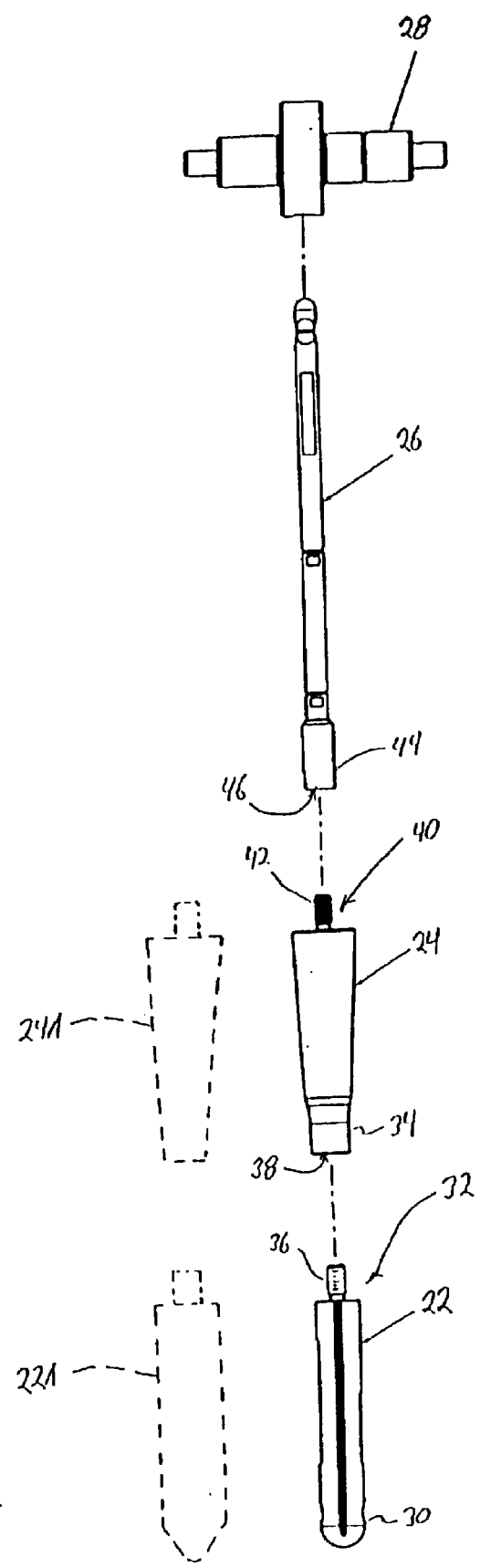
FIG. 2 is an exploded view of the instrument illustrated in FIG. 1.

As illustrated best in FIG. 2, each of the components may be selectively separated to permit the removal and/or substitution of desired components. As illustrated, trial stem 22 comprises a distal end 30 designed for insertion into the bone. (It should be noted that end 30 is described as a distal end because the illustrated instrument is for use on the proximal tibia. However, the lead end 30 could actually be the proximal end when the instrument is designed for other joint locations.) Trial stem 22 also comprises a proximal coupling end 32 designed for connection to bone impaction preform 24 or other components, such as trial stem adapter 26.

Bone impaction preform 24 includes a distal coupling end 34 designed to engage proximal coupling end 32 of trial stem 22. A variety of mechanisms can be utilized to permit selective coupling of preform 24 with trial stem 22. However, one exemplary design utilizes a threaded protrusion 36 extending axially at proximal coupling end 32 for receipt in a corresponding threaded opening 38 of distal coupling end 34.

Regardless of the specific coupling mechanism, the modular design facilitates the assembly of a desired bone impaction instrument by permitting selection of interchangeable trial stems, e.g., trial stem 22A, and interchangeable bone impaction to preforms, e.g., preform 24A.

Bone impaction preform 24 also may be designed for selective coupling with trial stem adapter 26. In the embodiment illustrated, preform 24 includes a proximal coupling end 40 having, for example, a threaded protrusion 42. Trial stem adapter 26 has a corresponding distal coupling end 44 with a threaded, axial opening 46 for threadably receiving protrusion 42. Thus, trial stem 22, bone impaction preform 24, and trial stem adapter 26 may be readily connected and disconnected to permit the substitution and removal of components to adjust parameters for a given procedure or patient.

In the illustrated embodiment, handle 28 also may be selectively attached and detached from trial stem adapter 26. An exemplary handle for use with the instrument is a quick-release handle as known to those of ordinary skill in the art.

Bone impaction preform 24 is designed for preforming an appropriate opening in bone replacement material impacted in a void at the proximal end of a tibia. In other words, the preform is generally of the size and shape of a tibial boss portion of an implantable prosthetic component, as will be explained more fully below. Bone impaction preform 24 has an outer surface that tapers generally radially outwardly intermediate distal coupling end 34 and proximal coupling end 40. Specifically, the maximum diameter of bone impaction preform 24 is greater than the maximum diameter of trial stem 22 and, in this embodiment, the diameter of bone impaction preform 24 increases moving from distal coupling end 34 towards proximal coupling end 40.

Figures 3, 4:
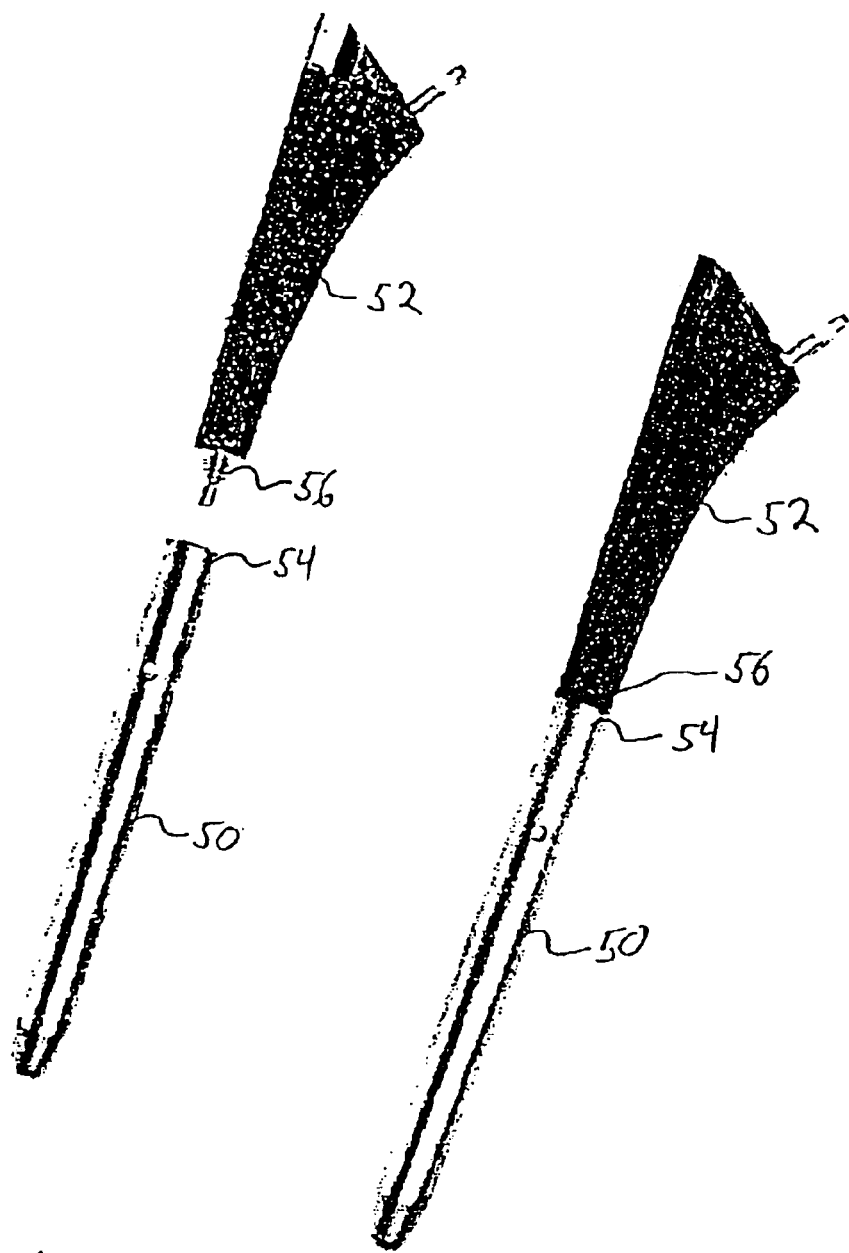
FIG. 3 is an alternate embodiment of the instrument illustrated in FIG. 1.
FIG. 4 is an exploded view of the instrument illustrated in FIG. 3.

It should be noted that the actual configuration of bone impaction preform 24 can be adjusted according to the shape of the component to be implanted. Additionally, the shape of bone impaction preform 24 typically varies when used at other skeletal locations. For example, a modular system for use at a proximal femur location for repair of a hip joint is illustrated in FIGS. 3 and 4. In this embodiment, a trial stem 50 may be selectively coupled to a bone impaction preform 52 via a proximal coupling end 54 of trial stem 50 and a distal coupling end 56 of preform 52. In this design, preform 52 expands outwardly from trial stem 50 such that the cross sectional area of preform 52 increases moving in the direction away from trial stem 50. However, the overall shape of preform 52 is substantially different than that of bone impaction preform 24 to accommodate specific implantable prosthetic components used in a hip or partial hip replacement. A wide variety of trial stems and preforms can be adapted to the desired shape of prosthetic components implanted at a given joint.

Figure 5:
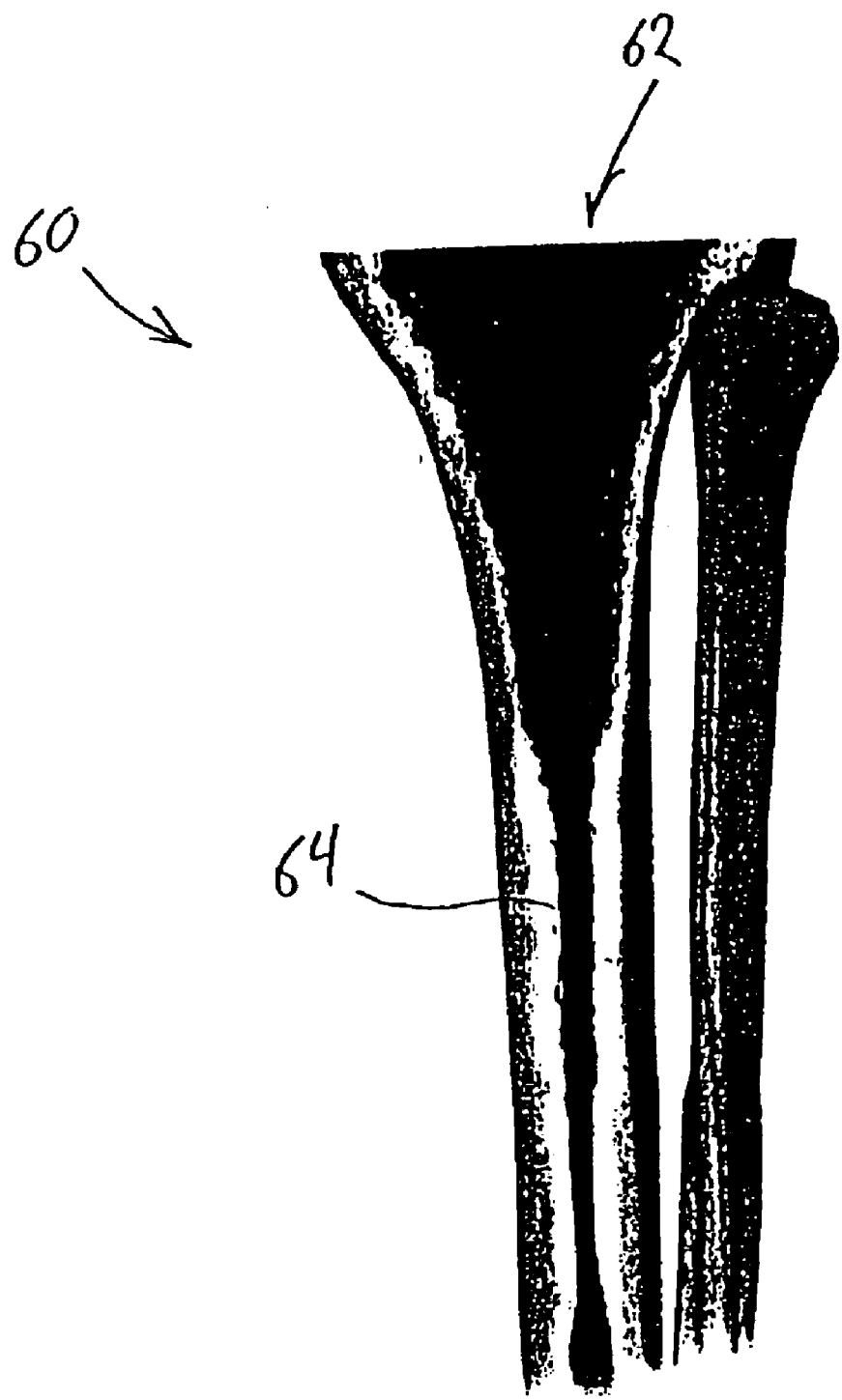
FIG. 5 illustrates a bone, e.g., the proximal end of a tibia, having a void to be filled with bone replacement material prior to implantation of an orthopedic prosthetic component.

An exemplary implementation of bone impaction instrument 20 will now be described with reference to an exemplary proximal tibia being prepared for implantation of a prosthetic component. As illustrated in FIG. 5, a proximal tibial region 60 has a void 62 created by a deterioration of the bone tissue. Void 62 may comprise a cavitary or non-cavitary void that must be filled with appropriate bone replacement material to support the prosthetic component. Void 62 leads to a medullary canal 64 generally at the longitudinal center of the bone.

Figure 6:
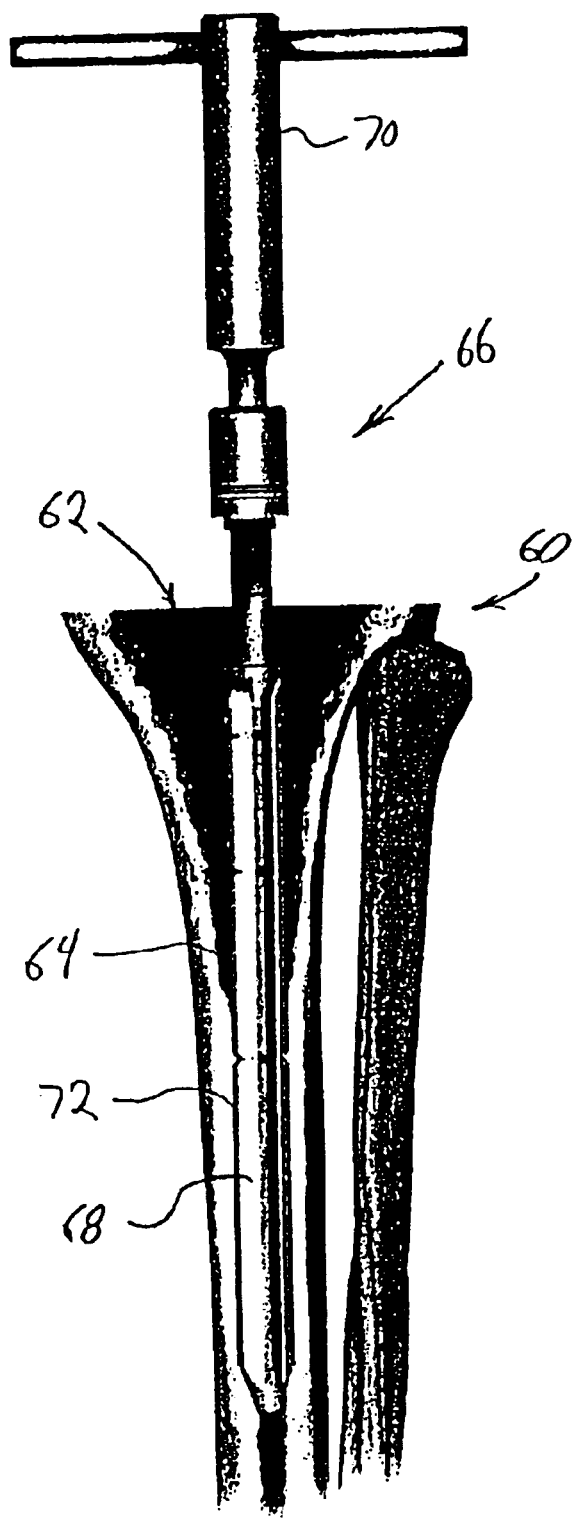
FIG. 6 illustrates the use of a reamer for reaming a portion of the medullary canal of the bone illustrated in FIG. 5.

Initially, a reamer 66 having a cutter portion 68 and a handle 70 is used to remove bone for receipt of an implant stem, as illustrated in FIG. 6. Specifically, the cutter portion is inserted into canal 64 and rotated to remove bone tissue and form a reamed region 72. Preferably, the tissue is sufficiently removed to expose hard, cortical bone.

Figure 7:
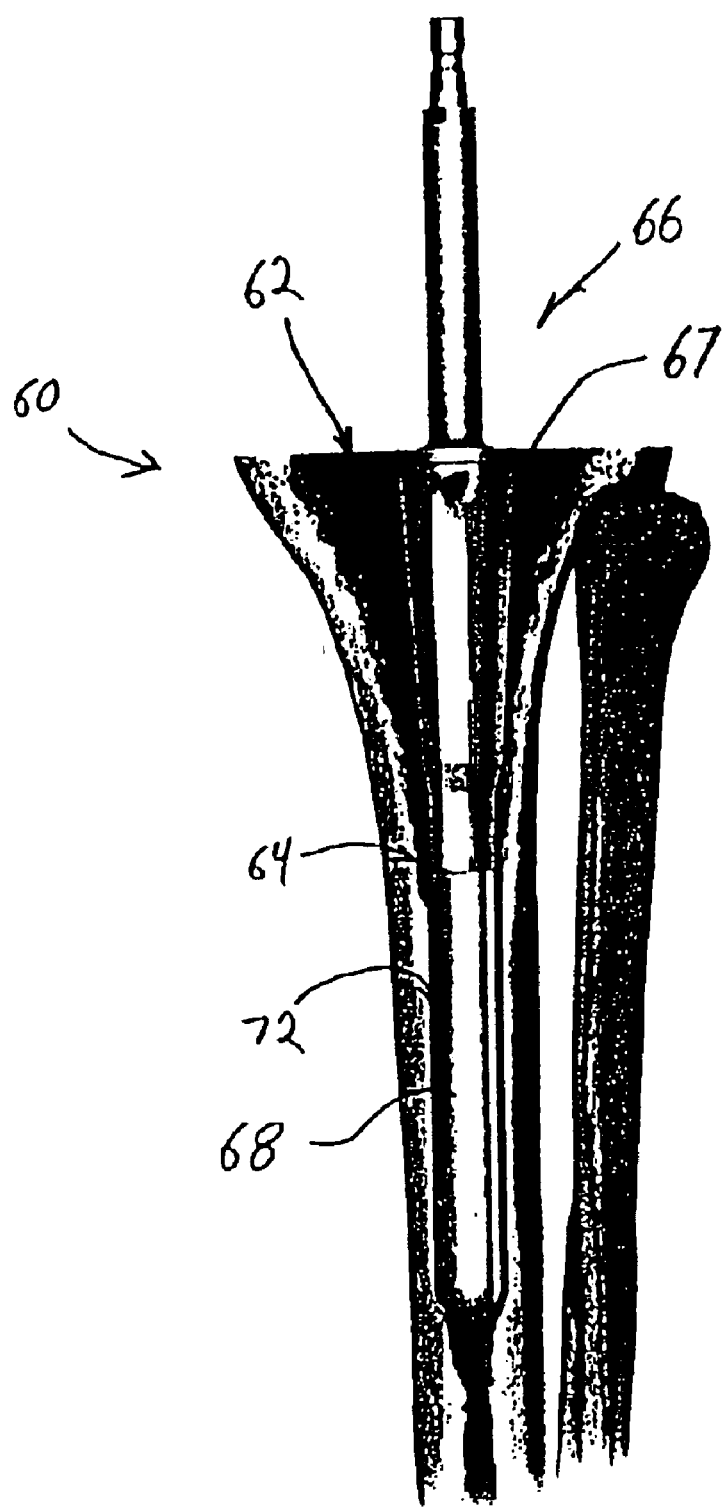
FIG. 7 illustrates the use of a cone reamer for removing bone material that would interfere with the preform and the prosthetic component to be implanted.
Figure 8:
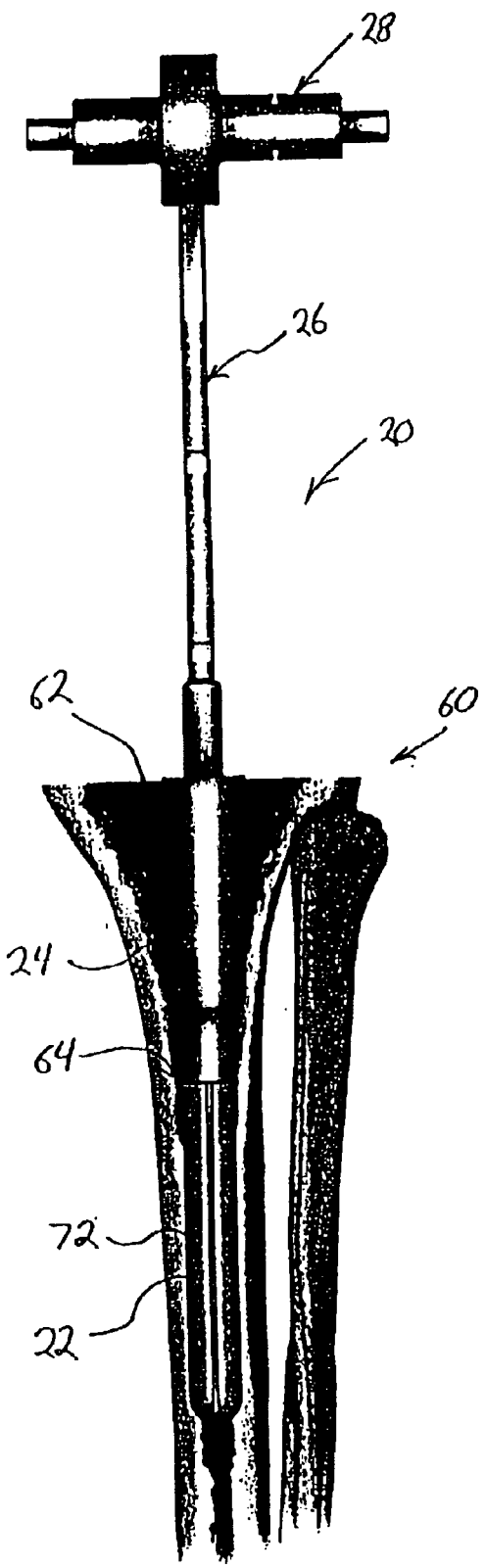
FIG. 8 illustrates the instrument of FIG. 1 disposed within the proximal end of a tibia.

If bone tissue interferes with the positioning of preform 24 and the subsequent prosthetic component, an additional reamer, such as a cone reamer 67, may be used in the area of void 62, as illustrated in FIG. 7. Cone reamer 67 also may be moved, e.g., rotated, by handle 70 until the area is cleared for bone impaction preform 24. Once cleared, cone reamer 67 is pulled from void 62 and bone impaction instrument 20 is moved into position. Handle 28 and trial stem adapter 26 are used by the practitioner to insert trial stem 22 into the reamed region 72 of canal 64. Trial stem 22 is positioned such that preform 24 is disposed at least partially within void 62, as illustrated best in FIG. 8.

Figure 9:
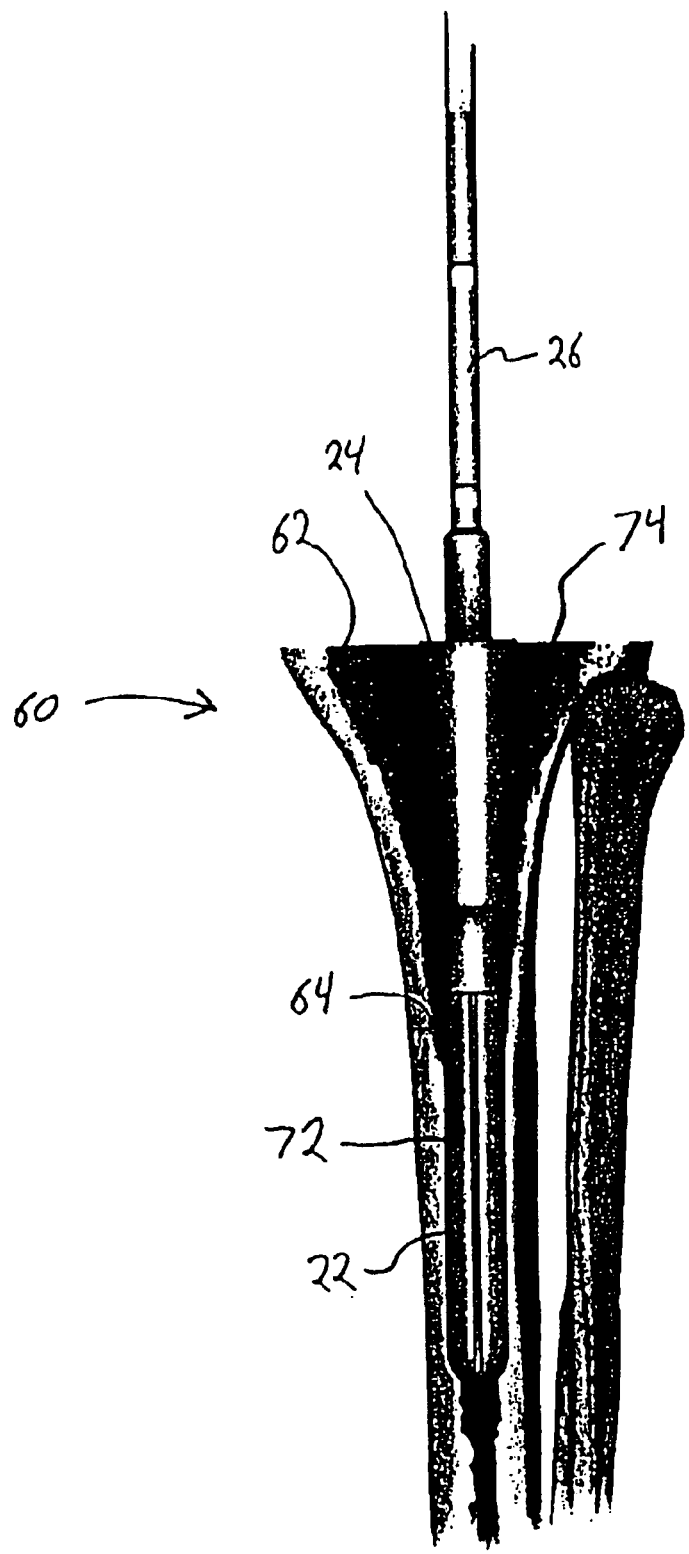
FIG. 9 is similar to FIG. 8 except for removal of the instrument handle.

Subsequently, handle 28 is removed from trial stem adapter 26 (see FIG. 9) and a bone replacement material 74 is disposed in void 62 and impacted around bone impaction preform 24. An exemplary bone replacement material may be a granulated bone structure, such as allograft bone, autograft bone, bone graft substitutes, bone matrix, or other suitable bone replacement materials. At this point, handle 28 may be reattached to trial stem adapter 26 for removal of preform 24 and trial stem 22. The preform 24 and trial stem 22 are then pulled from void 62 and reamed region 72 for insertion of a suitable orthopedic prosthetic component.

Figure 10:
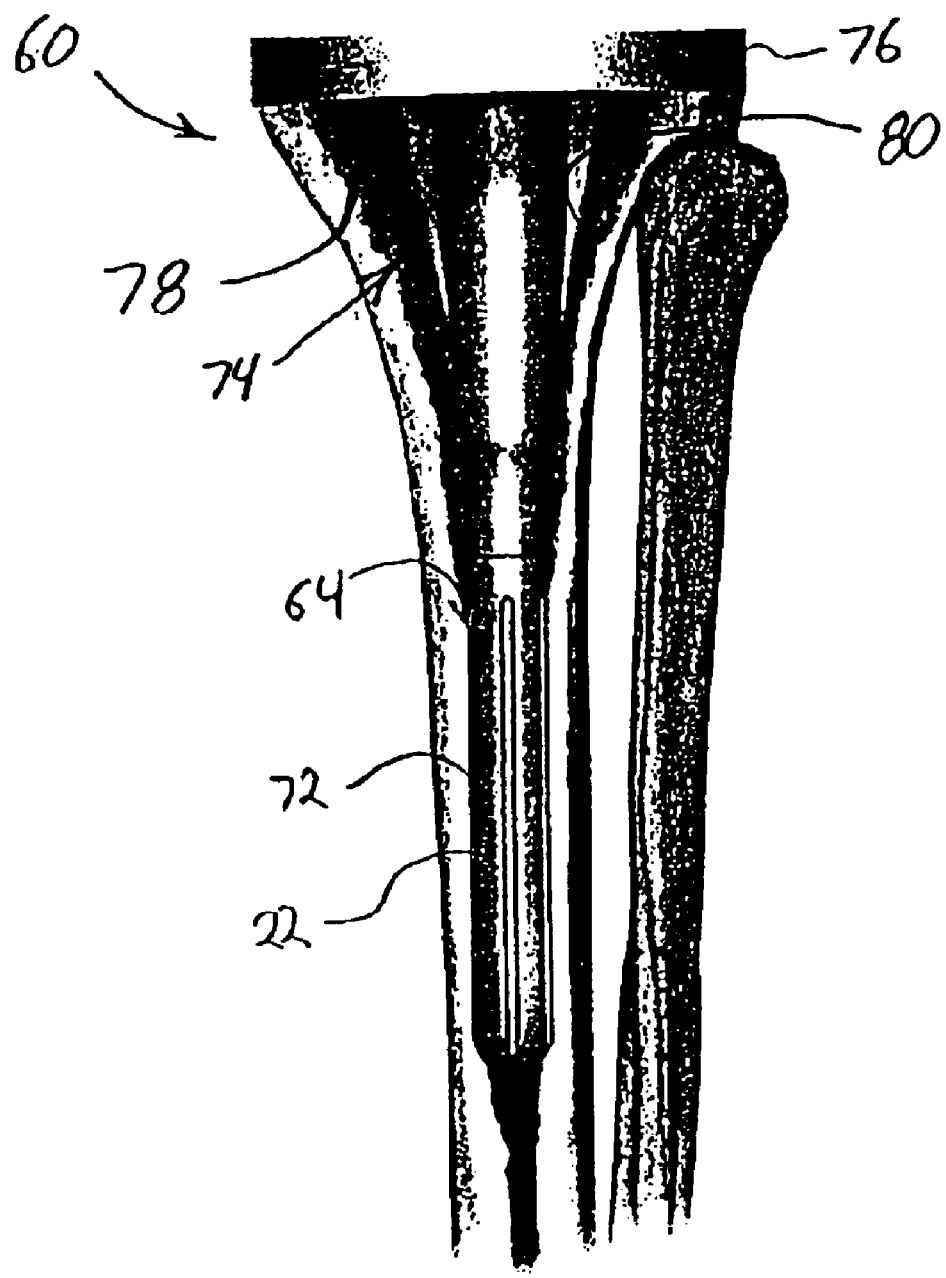
FIG. 10 illustrates one example of additional preparation of the bone replacement material to accommodate a particular orthopedic prosthetic component.

However, certain procedures may require additional preparation of proximal tibia 60 and bone replacement material 74. For example, in this exemplary implantation procedure, a trial tibia base plate 76, and the trial stem 22 are inserted into the cavity formed in bone replacement material 74. Once trial tibia base plate 76 is properly positioned at the pre-prepared end of proximal tibia 60, additional bone replacement material formation procedures can be performed, if necessary, to accommodate the particular shape of a prosthetic device. For example, in the embodiment illustrated in FIG. 10, a keel broach 78 is inserted through trial tibia base plate 76 to create a keel geometry within bone replacement material 74. This is just one example of a variety of finishing steps that may be conducted with respect to either the tissue itself or the bone replacement material.

Once the proper geometry is created in bone replacement material 74, a trial reduction may be performed. Typically, a trial reduction is used to check the movement of other prosthetic joint components with the various trial components in place. Subsequently, the trial tibia base plate 76, keel broach 78 and trial stem 22 are removed to leave reamed region 72 along with a preformed cavity region 80 within impacted bone replacement material 74.

The prosthetic component to be implanted is then cemented and moved into the appropriately shaped cavity region 80 and reamed region 72. In the particular example discussed, the implanted component would have a stem corresponding to trial stem 22 and a tibial boss corresponding to the shape of preform 24 and keel broach 78. It should be noted that this same procedure for forming an appropriate receptacle to receive an implantable component also can be utilized with cementless applications.

It will be understood that the foregoing description is of exemplary embodiments of this invention, and that the invention is not limited to the specific form shown. For example, the modular bone impaction instrument can be designed for use at a variety of joints other than those illustrated and discussed herein. The shape and configuration of the trial stem and bone impaction preform can be adjusted to correspond with the specific design of the component to be implanted. The procedural steps discussed above for use of the bone impaction instrument may be altered depending on the particular procedure. For example, a variety of other preparation steps, including bone cutting and other bone formation techniques may be utilized in preparing the tissue for attachment of the orthopedic prosthetic device. These and other modifications may be made in the design and arrangement of the elements without departing from the scope of the invention as expressed in the dependent claims.

What is claimed is:

1. A method of preparing a bone having a void for receipt of an implantable prosthetic device, comprising:
    selecting a desired combination of a modular trial stem and a modular preform;
    reaming an inner region of a bone to form a reamed region of sufficient size to accommodate a stem of an implantable prosthetic device;
    moving the modular trial stem into the reamed region until the preform is at least partially positioned in the void; and
    packing a bone replacement material around the modular preform.

2. The method as recited in claim 1, further comprising attaching a modular trial stem adapter to the modular preform.

3. The method as recited in claim 2, further comprising attaching a releasable handle to the trial stem adaptor prior to moving the modular trial stem into the reamed region.

4. The method as recited in claim 1, further comprising removing interfering bone along the void with a cone reamer.

5. The method as recited in claim 1, further comprising removing the modular trial stem prior to implantation of the implantable prosthetic device.

6. The method as recited in claim 5, further comprising disassembling the modular trial stem and the modular preform.

* * * * *